(12) United States Patent
Hada et al.

(10) Patent No.: US 6,720,534 B2
(45) Date of Patent: Apr. 13, 2004

(54) POWER SUPPLY CONTROL SYSTEM FOR HEATER USED IN GAS SENSOR

(75) Inventors: Satoshi Hada, Inazawa (JP); Eiichi Kurokawa, Okazaki (JP); Akio Tanaka, Gifu (JP)

(73) Assignee: Denso Corporation, Kariya (JP)

( * ) Notice: Subject to any disclaimer, the term of this patent is extended or adjusted under 35 U.S.C. 154(b) by 29 days.

(21) Appl. No.: 10/158,110

(22) Filed: May 31, 2002

(65) Prior Publication Data

US 2002/0179594 A1 Dec. 5, 2002

(30) Foreign Application Priority Data

May 31, 2001 (JP) .......................... 2001-164600
Apr. 9, 2002 (JP) .......................... 2002-106332

(51) Int. Cl.$^7$ .............................. H05B 1/02
(52) U.S. Cl. ........................ 219/494; 204/425
(58) Field of Search ................. 219/494, 497, 219/501, 505, 504; 204/424, 425; 123/434, 697

(56) References Cited

U.S. PATENT DOCUMENTS

| | | | | |
|---|---|---|---|---|
| 4,543,176 A | * | 9/1985 | Harada et al. ............... | 204/406 |
| 4,938,196 A | * | 7/1990 | Hoshi et al. ................ | 73/23.32 |
| 4,963,246 A | * | 10/1990 | Nakajima et al. ............ | 204/406 |
| 5,214,267 A | * | 5/1993 | Hoshi et al. ................ | 219/497 |
| 5,709,198 A | * | 1/1998 | Sagisaka et al. ............ | 123/684 |
| 5,731,570 A | * | 3/1998 | Aoki ......................... | 219/497 |
| 6,083,370 A |   | 7/2000 | Kato et al. | |
| 6,294,075 B1 | * | 9/2001 | Poggio et al. .............. | 205/785 |
| 6,540,892 B1 | * | 4/2003 | Strohmaier ................. | 204/408 |
| 6,578,563 B2 | * | 6/2003 | Hada et al. ................. | 123/697 |
| 6,586,711 B2 | * | 7/2003 | Whitney et al. ............. | 219/497 |
| 2002/0000436 A1 | * | 1/2002 | Hashimoto et al. ......... | 219/497 |

FOREIGN PATENT DOCUMENTS

| | | |
|---|---|---|
| JP | 10-232220 | 9/1998 |
| JP | 2001-74693 | 3/2001 |

* cited by examiner

Primary Examiner—John A. Jeffery
(74) Attorney, Agent, or Firm—Nixon & Vanderhye P.C.

(57) ABSTRACT

A heater control apparatus used for a gas concentration sensor heats a sensor element including a solid electrolyte body up to a desired activation temperature. The heater control apparatus determines an actual resistance value of the sensor element, controls a power supply to the heater as a function of a difference between the actual resistance value and a target one, determines a power supplied to the heater, and determines a reference resistance value of the sensor element based on a predetermined fundamental relation between a power used in the heater and a resistance value of the sensor element to correct the target resistance value as a function of a difference between the reference resistance value and the actual resistance value.

24 Claims, 9 Drawing Sheets

POWER SUPPLY CONTROL SYSTEM FOR HEATER USED IN GAS SENSOR

BACKGROUND OF THE INVENTION

1. Technical Field of the Invention

The present invention relates generally to a power supply control system for a heater used to heat a gas sensor such as a gas concentration sensor up to a desired activation temperature which may be employed in an air-fuel ratio control system for automotive vehicles for measuring the concentration of gas such as $O_2$, NOx, or CO.

2. Background Art

Limiting current type gas concentration sensors are known which are used for measuring NOx contained in exhaust gasses of automotive engine. There is used one of such gas concentration sensors which includes a pump cell and a sensor cell. The pump cell works to pump oxygen ($O_2$) contained in gasses admitted into a gas chamber out of the sensor or to pump oxygen ($O_2$) of outside gasses into the gas chamber. The sensor cell works to measure the concentration of NOx contained in the gasses after passing through the pump cell. The pump cell and the sensor cell are designed to produce current signals indicative of the concentration of oxygen and NOx upon application of voltage thereto.

The above type of gas concentration sensors usually have disposed therein a heater for keeping the pump cell and the sensor cell at a desired activation temperature. The power supply to the heater is regulated under feedback control by monitoring the resistance value of a solid electrolyte body (which will also be referred to as a sensor element resistance value below) on which the pump cell and the sensor cell are disposed and determining the power supply so as to bring the monitored resistance value into agreement with a target one corresponding to the desired activation temperature.

An undesirable change in characteristic of the gas concentration sensor due to, for example, deterioration of the solid electrolyte body will, however, result in a shift between an actually controlled temperature of the pump and sensor cells (which will also be referred to as a sensor element temperature below) and the desired activation temperature. This may cause the pump and sensor cells to be overheated or less heated, so that they are kept out of the desired activation temperature, which will result in an undesirable variation in amount of oxygen pumped by the pump cell, thus leading to a great error in determining the concentrations of oxygen and NOx.

Specifically, when the sensor element temperature is increased above the desired activation temperature, it will cause the pump cell to dissociate NOx as well as oxygen within the gas chamber, which will cause the concentration of NOx to be determined as being lower than an actual value. Alternatively, when the sensor element temperature is decreased below the desired activation temperature, it will cause the pump cell to dissociate oxygen incompletely, which will result in an increase in amount of oxygen remaining within the gas chamber. The amount of oxygen dissociated by the sensor cell together with NOx is, thus, increased, thereby causing the concentration of NOx to be determined as being higher than an actual value.

Usually, the pump cell produces a current of several mA indicative of the concentration of oxygen, while the sensor cell produces a current of several $\mu A$ indicative of the concentration of NOx. A shift in amount of oxygen pumped by the pump cell from a target one, therefore, result in a great error in determining the concentration of NOx using the current produced by the sensor cell.

SUMMARY OF THE INVENTION

It is therefore a principal object of the present invention to avoid the disadvantages of the prior art.

It is another object of the present invention to provide a heater control system for a gas concentration measuring apparatus which is designed to keep a gas concentration sensor at a desired activation temperature, thereby ensuring required measurement accuracy of the gas concentration measuring apparatus.

According to one aspect of the invention, there is provided a heater control apparatus for a gas concentration measuring system which may be employed with an automotive control system designed to control the quantity of fuel injected into an internal combustion gasoline engine as a function of an output of the gas concentration measuring system under feedback (F/B) control to bring the air-fuel (A/F) ratio into agreement with a target value. The gas concentration measuring system has a gas concentration sensor which consists essentially of a gas chamber, a first cell working to pump thereinto oxygen molecules contained in gasses admitted into the gas chamber and discharge the pumped oxygen molecules, a second cell working to determine a concentration of a specified oxygen containing gas component contained in the gasses having passed through the first cell, a solid electrolyte member on which at least one of the first and second cells is disposed, and a heater heating the first and the second cells. The heater control apparatus comprising: (a) a sensor element resistance value determining circuit working to applying one of a varying voltage and a varying current to the solid electrolyte member and measuring resulting changes in voltage appearing across the solid electrolyte member and current flowing through the solid electrolyte member to determine a resistance value of a sensor element including the solid electrolyte member; (b) a heater control circuit controlling a power supply to the heater as a function of a difference between the resistance value determined by the sensor element resistance value determining circuit and a target resistance value; (c) a heater power determining circuit determining a power supplied to the heater; and (d) a correcting circuit working to determine a reference resistance value of the sensor element as a function of the power determined by the heater power determining circuit based on a predetermined fundamental relation between a power used in the heater and a resistance value of the sensor element, the correcting circuit correcting the target resistance value as a function of the reference resistance value.

In the preferred mode of the invention, the correcting circuit corrects the target resistance value based on the reference resistance value and the resistance value determined by the sensor element resistance value determining circuit. Specifically, the correcting circuit may correct the target resistance value as a function of a difference between the reference resistance value and the resistance value determined by the sensor element impedance determining circuit.

The correcting circuit may reflect an external factor of a change in temperature of the sensor element in an environmental condition of the gas concentration sensor in correcting the target resistance value.

The correcting circuits may correct the target resistance value under condition that an external factor of a change in temperature of the sensor element is unchanged.

The gas concentration sensor may be installed in an exhaust pipe of an engine to measure and used in an engine control system working to detect exhaust gasses of the engine through the gas concentration sensor. The correcting circuit may correct the target resistance value under condition that the engine is at rest.

The degree to which the correcting circuit corrects the target resistance value may be stored in a backup memory as a learning value for use in correcting the target resistance value.

A measure of deterioration of the gas concentration sensor may be determined based on the degree to which the correcting circuit corrects the target resistance value.

According to the second aspect of the invention, there is provided a heater control apparatus for a gas concentration measuring system. The gas concentration system has a gas concentration sensor which consists essentially of a gas chamber, a first cell working to pump thereinto oxygen molecules contained in gasses admitted into the gas chamber and discharge the pumped oxygen molecules, a second cell working to determine a concentration of a specified oxygen containing gas component contained in the gasses having passed through the first cell, a solid electrolyte member on which at least one of the first and second cells is disposed, and a heater heating the first and the second cells. The heater control apparatus comprises: (a) a sensor element resistance value determining circuit working to applying one of a varying voltage and a varying current to the solid electrolyte member and measuring resulting changes in voltage appearing across the solid electrolyte member and current flowing through the solid electrolyte member to determine a resistance value of a sensor element including the solid electrolyte member; (b) a heater control circuit controlling a power supply to the heater as a function of a difference between the resistance value determined by the sensor element resistance value determining circuit and a target resistance value; (c) a heater resistance determining circuit determining a resistance value of the heater; and (d) a correcting circuit working to determine a reference resistance value of the sensor element as a function of the resistance value determined by the heater resistance determining circuit based on a predetermined fundamental relation between a resistance value of the heater and a resistance value of the sensor element, the correcting circuit correcting the target resistance value as a function of the reference resistance value.

In the preferred mode of the invention, the correcting circuit may correct the target resistance value as a function of a difference between the reference resistance value and the resistance value determined by the sensor element resistance value determining circuit.

The correcting circuit may reflect an external factor of a change in temperature of the sensor element in an environmental condition of the gas concentration sensor in correcting the target resistance value.

The correcting circuits may correct the target resistance value under condition that an external factor of a change in temperature of the sensor element is unchanged.

The gas concentration sensor may be installed in an exhaust pipe of an engine to measure and used in an engine control system working to detect exhaust gasses of the engine through the gas concentration sensor. The correcting circuit may correct the target resistance value under condition that the engine is at rest.

The degree to which the correcting circuit corrects the target resistance value may be stored in a backup memory as a learning value for use in correcting the target resistance value.

A measure of deterioration of the gas concentration sensor may be determined based on the degree to which the correcting circuit corrects the target resistance value.

According to the third aspect of the invention, there is provided a heater control apparatus for a gas concentration measuring system. The gas concentration system has a gas concentration sensor which consists essentially of a gas chamber, a first cell working to pump thereinto oxygen molecules contained in gasses admitted into the gas chamber and discharge the pumped oxygen molecules, a second cell working to determine a concentration of a specified oxygen containing gas component contained in the gasses having passed through the first cell, a solid electrolyte member on which at least one of the first and second cells is disposed, and a heater heating the first and the second cells, The heater control apparatus comprises: (a) a sensor element resistance value determining circuit working to applying one of a varying voltage and a varying current to the solid electrolyte member and measuring resulting changes in voltage appearing across the solid electrolyte member and current flowing through the solid electrolyte member to determine a resistance value of a sensor element including the solid electrolyte member; (b) a heater control circuit controlling a power supply to the heater as a function of a difference between the resistance value determined by the sensor element resistance value determining circuit and a target resistance value; (c) a sensor element temperature determining circuit determining a temperature of the sensor element; and (d) a correcting circuit working to determine a reference resistance value of the sensor element as a function of the temperature determined by the sensor element temperature determining circuit based on a predetermined fundamental relation between a temperature of the sensor element and a resistance value of the sensor element, the correcting circuit correcting the target resistance value as a function of the reference resistance value.

In the preferred mode of the invention, the gas concentration sensor may be installed in an exhaust pipe of an engine to measure and used in an engine control system designed to detect exhaust gasses of the engine. The sensor element temperature determining circuit may determine, as the temperature of the sensor element; one of an actual temperature of the sensor element and an estimate thereof based on one of a temperature and a flow rate of the exhaust gasses.

The control circuit controls the power supply to the heater to bring a temperature of the sensor element into agreement with a target controlled temperature. The sensor element temperature determining circuit determines two temperatures of the sensor element defined across the target controlled temperature. The correcting circuit determines two reference resistance values corresponding to the two temperatures of the sensor element by look-up using the predetermined fundamental relation and corrects the target resistance value using the two temperatures of the sensor element and the two reference resistance values.

The correcting circuit corrects the target resistance value as a function of a difference between the reference resistance value and the resistance value determined by the sensor element resistance value determining circuit.

The correcting circuit may reflect an external factor of a change in temperature of the sensor element in an environmental condition of the gas concentration sensor in correcting the target resistance value.

The correcting circuits may correct the target resistance value under condition that an external factor of a change in temperature of the sensor element is unchanged.

In a case where the gas concentration sensor is installed in the exhaust pipe of the engine and used in the engine control system, the correcting circuit may correct the target resistance value under condition that the engine is at rest.

The degree to which the correcting circuit corrects the target resistance value may be stored in a backup memory as a learning value for use in correcting the target resistance value.

A measure of deterioration of the gas concentration sensor may be determined based on the degree to which the correcting circuit corrects the target resistance value.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
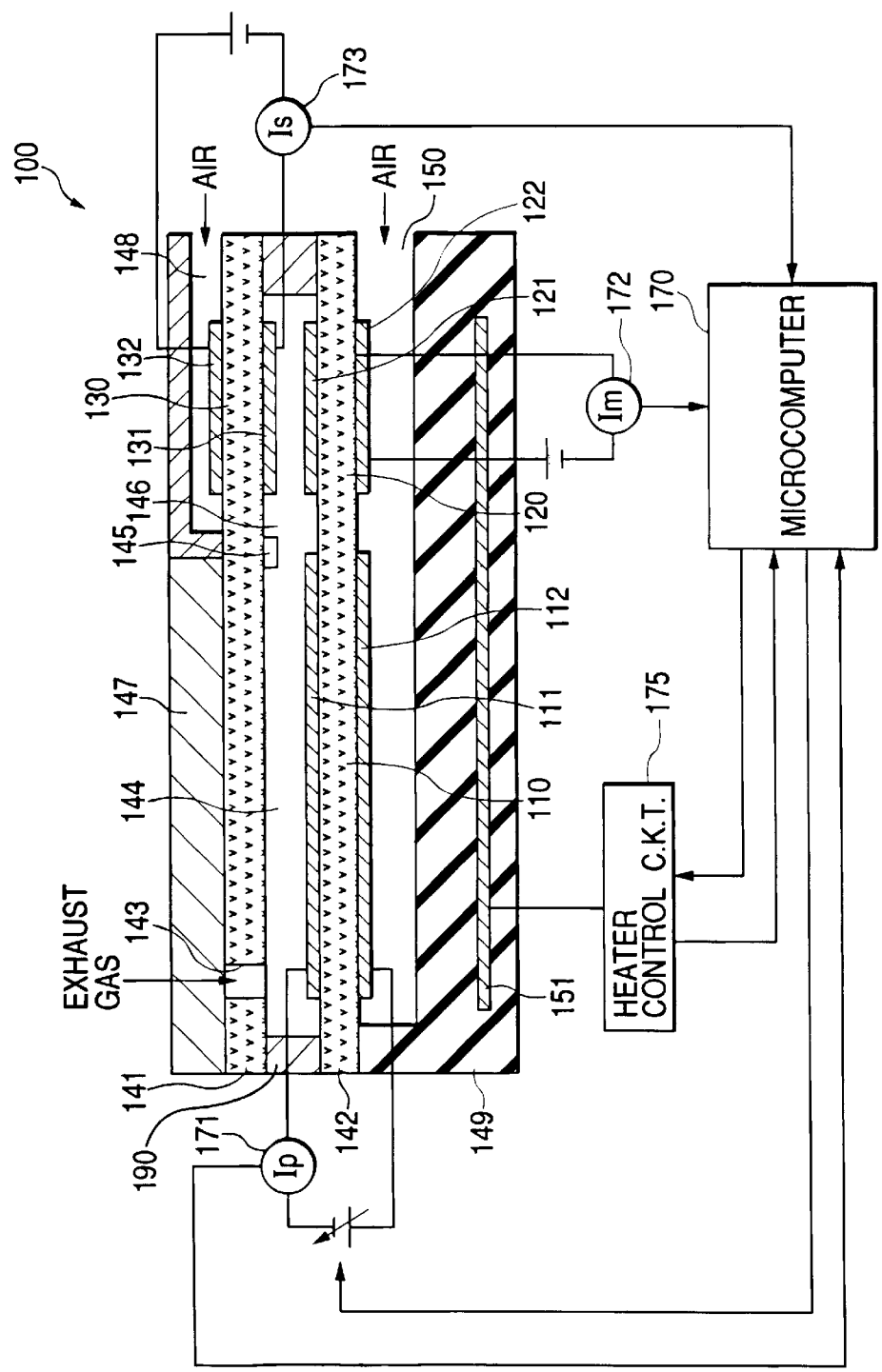
FIG. 1 is a block diagram which shows a gas concentration measuring apparatus according to the first embodiment of the invention.

Referring now to the drawings, wherein like numbers refer to like parts in several views, particularly to FIG. 1, there is shown a gas concentration measuring apparatus according to the first embodiment of the invention which may be used with an automotive control system designed to control the quantity of fuel injected into an internal combustion gasoline engine as a function of an output of the gas concentration measuring apparatus under feedback (F/B) control to bring the air-fuel (A/F) ratio into agreement with a target value. The gas concentration measuring apparatus uses a composite gas sensor to measure concentrations of oxygen ($O_2$) and nitrogen oxide (NOx) contained in exhaust gasses of the internal combustion engine simultaneously and has disposed therein a heater control system which works to control a power supply to a heater built in the gas sensor to keep a sensor element in a desired activation condition.

The gas concentration measuring apparatus, as shown in FIG. 1, generally includes a gas concentration sensor 100, a microcomputer or controller 170, and current detectors 171, 172, and 173 (e.g., ammeters).

The following discussion will refer to an example in which the gas concentration sensor 100 is installed in an exhaust pipe of an automotive internal combustion engine.

The gas concentration sensor 100 generally includes solid electrolyte plates 141 and 142 made of an oxygen ion-conducting material. The solid electrolyte plates 141 and 142 are laid to overlap each other at a given interval through a spacer 190 made of an insulating material such as alumina. The solid electrolyte plate 141 has formed therein a pinhole 143 through which exhaust gasses flowing around the gas concentration sensor 100 are admitted into a first chamber 144. The first chamber 144 communicates with a second chamber 146 through an orifice 145 working as a diffusion path. On the solid electrolyte plate 141, a porous diffusion layer 147 is formed.

The solid electrolyte plate 142 has formed therein a pump cell 110 and a monitor cell 120. The pump cell 110 works to dissociate or ionize and pump thereinto oxygen molecules ($O_2$) contained the exhaust gasses admitted into the first chamber 144 and discharge them for measuring the concentration of oxygen ($O_2$) contained in the exhaust gasses and also to dissociate or ionize and pump oxygen molecules ($O_2$) within an air passage 150 into the first chamber 144 when the concentration of oxygen within the first chamber 144 is lower than a given level for keeping the concentration of oxygen within the first chamber 144 at the given level. The monitor cell 120 works to produce an electromotive force or current upon application of the voltage as a function the concentration of oxygen ($O_2$) within the second chamber 146. The pump cell 110 has a pair of upper and lower electrodes 111 and 112 disposed on opposed surfaces thereof. The upper electrode 111 is exposed to the first chamber 144 and inactive with respect to NOx, that is, hardly decomposes NOx. Similarly, the monitor cell 120 has a pair of upper and lower electrodes 121 and 122 disposed on opposed surfaces thereof. The upper electrode 121 is exposed to the second chamber 146 and inactive with respect NOx, like the electrode 111. The pump cell 110 and the monitor cell 120 work to pump $O_2$ molecules contained in the exhaust gasses out of the first and second chambers 144 and 146 and discharge them to the air passage 150 through the electrodes 112 and 122.

A sensor cell 130 is formed in the solid electrolyte plate 144 opposite the monitor cell 120 and has a pair of upper and lower electrodes 131 and 132 formed on opposed surfaces thereof. The sensor cell 130 serves to measure the concentration of NOx contained in the exhaust gasses having passed through the pump cell 110 and discharge the oxygen produced when NOx is decomposed within the second chamber 146 to the air passage 148 through the electrode 132.

An insulating layer 149 is disposed on a lower surface, as viewed in FIG. 1, of the solid electrolyte plate 142 to define the air passage 150. The insulating layer 149 has embedded therein a heater 151 for heating the whole of the sensor 100 up to a given temperature.

In operation, when exhaust gasses containing $O_2$, NOx, $CO_2$, and $H_2O$ enter the first chamber 144 through the porous diffusion layer 147 and the pinhole 143 and are passing through the pump cell 110, application of voltage to the pump cell 110 through the electrodes 111 and 112 causes the exhaust gasses to undergo dissociation, so that the oxygen ($O_2$) is pumped into or out of the first chamber 144 as a function of the concentration of oxygen ($O_2$) within the first chamber 144 so as to keep the concentration of oxygen within the first chamber 144 constant. Since the upper electrode 111 of the pump cell 110 is, as described above, made of a metal which hardly decomposes NOx, when the concentration of oxygen within the first chamber 144 is higher than a desired level, only $O_2$ molecules within the first chamber 144 are ionized by the pump cell 110 without decomposing NOx, which are, in turn, discharged to the air passage 150. This causes a current (will also referred to as a pump cell current below) to be produced in the pump cell 110 as a function of the oxygen content of the exhaust gasses. EP0 987 546 A2, assigned to the same assignee as that of this application, teaches control of an operation of this type of gas sensor, disclosure of which is incorporated herein by reference.

The $O_2$ molecules in the exhaust gasses are usually not dissociated by the pump cell 110 completely, so that residual $O_2$ molecules flows into the second chamber 146 and reach the monitor cell 120. The application of given voltage to the monitor cell 120 through the electrodes 121 and 122 causes an output (will also be referred to as a monitor cell current below) to be produced as a function of the concentration of the residual oxygen. The application of given voltage to the sensor cell 130 through the electrodes 131 and 132 causes NOx molecules contained in the exhaust gasses to be decomposed or reduced, so that oxygen ions are produced and discharged to the air passage 148, thereby causing a current (also referred to as a sensor cell current or a NOx current below) to flow through the sensor 130 as a function of the concentration of NOx within the second chamber 146.

Figure 2A:
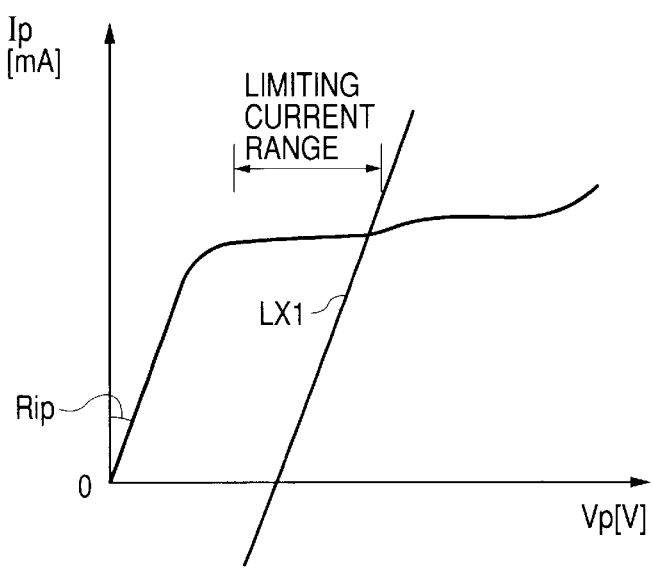
FIG. 2(a) is a graph which shows an example of a map listing an applied voltage-to-output current relation of a pump cell.
Figure 2B:
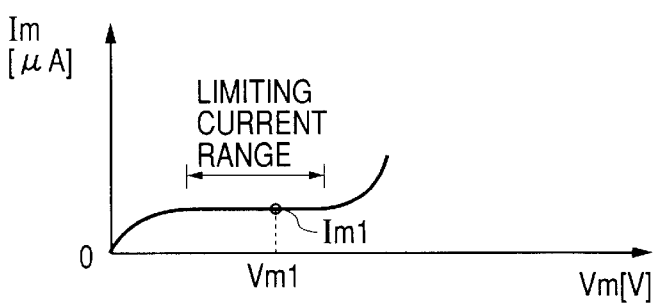
FIG. 2(b) is a graph which shows an example of a map listing an applied voltage-to-output current relation of a monitor cell.
Figure 2C:
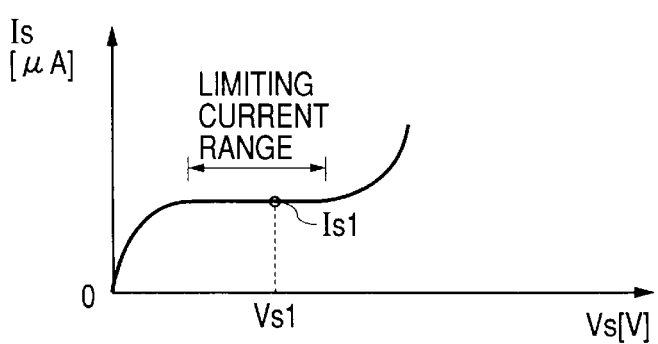
FIG. 2(c) is a graph which shows an example of a map listing an applied voltage-to-output current relation of a sensor cell.

FIGS. 2($a$), 2($b$), and 2($c$) show examples of V-I relations between the voltages applied to the pump cell 110, the monitor cell 120, and the sensor cell 130 and outputs thereof:: the pump cell current, the monitor cell current, and the sensor cell current, respectively. Note that FIGS. 2($a$) to 2($c$) illustrate sensor output characteristics when the concentration of $O_2$ and NOx are constant.

The pump cell 110 works to produce a limiting current as a function of the concentration of oxygen ($O_2$) within the first chamber 144. A straight segment of a curve, as shown in FIG. 2($a$), inclined slightly upward with respect to a V-axis (i.e., abscissa axis) indicates a limiting current measuring range in which the limiting current produced by the pump cell 110 is to be measured. The limiting current measuring range is shifted to the positive side of voltage applied to the pump cell 110 as the concentration of oxygen increases. This limiting current characteristics has a resistance-dependent range defined by a segment of the curve extending upward at an inclination substantially depending upon an impedance Rip of the pump cell 110 (i.e., the solid electrolyte plate 142).

The gas concentration measuring apparatus of this embodiment stores therein a V-Imap such as the one of FIG. 2($a$) and monitors the pump cell current Ip to determine the pump cell-applied voltage Vp to be applied to the pump cell 110 by look-up using the V-Imap. The V-Imap has a target applying voltage line LX1 and is used in determining the pump cell-applied voltage Vp along the line LX1. The upper pump cell electrode 111 of the pump cell 110 exposed to the first chamber 144 is, as described above, made of material which hardly decomposes NOx, so that NOx molecules in the exhaust gasses are hardly decomposed, but if the voltage applied to the pump cell 110 exceeds a certain upper limit, it will cause the NOx molecules to be decomposed, thereby producing an error in the pump cell current Ip (i.e., the limiting current) outputted from the pump cell 110. In practice, the target applying voltage line LX1 is so defined as to keep the concentration of oxygen ($O_2$) within the first chamber 144 at a lower level (near the stoichiometric). For instance, the target applying voltage line LX1 is so defined that a small quantity of $O_2$ (e.g., several ppm to several tens ppm) remains in the first chamber 144.

The monitor cell 120, like the pump cell 110, works to produce a limiting current as a function of the concentration of oxygen ($O_2$) within the second chamber 146. The application of a given voltage Vm1, as shown in FIG. 2($b$), to the monitor cell 120 causes a current Im1 to be produced. When the concentration of oxygen within the second chamber 146 is also kept at a lower level, e.g., several ppm to several tens ppm, by the activity of the pump cell 110, the monitor cell 120 produces a monitor cell current Im of the order of 0.5 to 2 $\mu$A.

The sensor cell 130 works to produce a limiting current as a function of the concentration of NOx. Specifically, the sensor cell 130 provides an output as a function of the concentration of NOx contained in the gasses within the second chamber 146. The application of a given voltage Vs1, as shown in FIG. 2($c$), to the sensor cell 130 causes a current Is1 to be produced.

Returning back to FIG. 1, the microcomputer 170 is implemented by a typical arithmetic logic unit consisting of a CPU, a memory, an A/D converter, a D/A converter, etc.

Power supply circuits are, as clearly shown in the drawing, provided one for each of the pump cell 110, the monitor cell 120, and the sensor cell 130. The power supply circuits include voltage sources for applying the voltages Vp, Vm, and Vs to the pump cell 110, the monitor cell 120, and the sensor cell 130 and the current detectors 171, 172, and 173, respectively. The current detector 171 measures the pump cell current Ip produced by the pump cell 110 and provides a signal indicative thereof to the microcomputer 170. The current detector 172 measures the monitor cell current Im produced by the monitor cell 120 and provides a signal indicative thereof to the microcomputer 170. The current detector 173 measures the sensor cell current Is produced by the sensor cell 130 and provides a signal indicative thereof to the microcomputer 170.

The microcomputer 170 receives the output from the current detector 171 of the pump cell 110 indicative of the pump cell current Ip and determines the concentration of oxygen ($O_2$) in the exhaust gasses to calculate an air-fuel (A/F) ratio. The microcomputer 170 also determines the pump cell-applied voltage Vp to be applied to the pump cell 110 using the target applying voltage line LX1 in the map of FIG. 2(a) as a function of the pump cell current Ip. The pump cell-applied voltage Vp is selected so as not to decompose NOx through the pump cell 110. Further, the microcomputer 170 corrects the pump cell-applied voltage characteristics using the monitor cell current Im measured by the current detector 172 and determines the concentration of NOx using the sensor cell current Is measured by the current detector 173.

The microcomputer 170 measures the impedance of the pump cell 110 using the sweep method. The measurement of the impedance is, as described later, achieved by changing the pump cell-applied voltage Vp to either of positive and negative sides instantaneously to produce an ac voltage which is, in turn, applied to the pump cell 110. The microcomputer 170 monitors changes in the voltage and the pump cell current Ip to calculate the impedance of the pump cell 110. The heater 151 is supplied with power from a storage battery installed in the vehicle.

Figure 3:
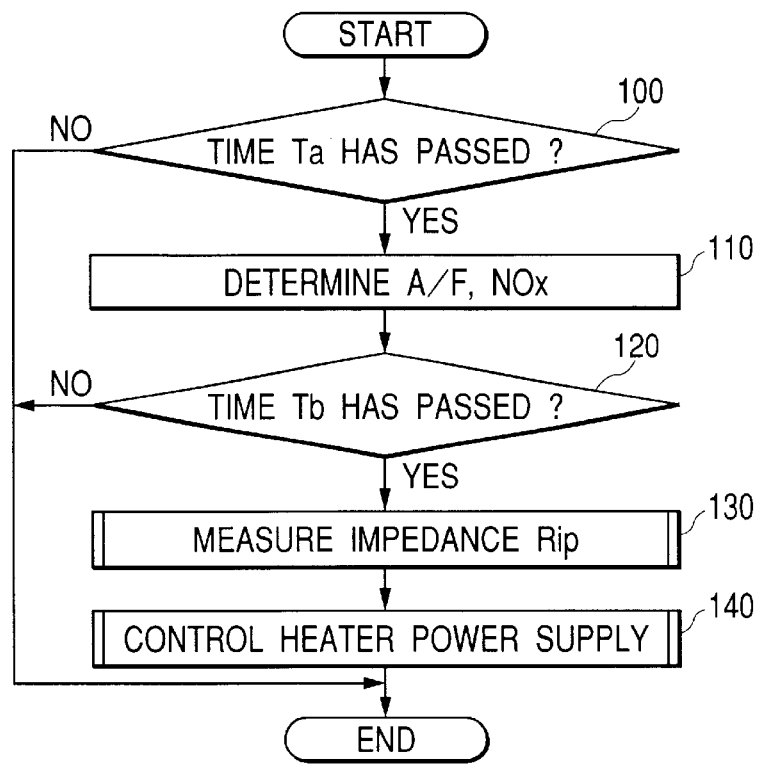
FIG. 3 is a flowchart of a main program executed to control a power supply to a heater built in a gas concentration sensor.

FIG. 3 is a flowchart of a maim program performed by the microcomputer 170 upon turning on thereof.

After entering the program, the routine proceeds to step 100 wherein it is determined whether a preselected period of time Ta has passed after previous measurement of the air-fuel ratio and NOx or not. The preselected period of time Ta corresponds to a measurement cycle of the air-fuel ratio and NOx and is, for example, 4 ms. If a NO answer is obtained in step 100, then the routine repeats step 100. Alternatively, if a YES answer is obtained, then the routine proceeds to step 110 for determining the air-fuel ratio and the concentration of NOx.

In step 110, the microcomputer 20 determines the voltage Vp to be applied to the pump cell 110 as a function of the measured pump cell current Ip and applies it to monitor a resulting value of the pump cell current Ip. The microcomputer 20 converts the monitored pump cell current Ip into a signal indicative of an air-fuel ratio. Additionally, the microcomputer 20 also determines the voltage Vs to be applied to the sensor cell 130 as a function of the measured sensor cell current Is and applies it to monitor a resulting value of the sensor cell current Is. The microcomputer 20 converts the monitored sensor cell current Is into a signal indicative of the concentration of NOx.

The routine proceeds to step 120 wherein it is determined whether a preselected period of time Tb has passed or not since the sensor element impedance Rip, as will be discussed later in detail, was measured previously. The preselected period of time Tb corresponds to a measurement cycle of the sensor element impedance Rip and is determined depending upon, for example, operating conditions of the engine. For example, when the engine is in a normal operating condition in which a change in air-fuel ratio is relatively small, Tb=2 sec. When the engine is in a start-up and transient conditions in which the air-fuel ratio changes greatly, Tb=128 msec.

If a YES answer is obtained in step 120, then the routine proceeds to step 130 wherein the sensor element impedance Rip is determined using a so-called sweep method. The routine proceeds to step 140 wherein a power supply to the heater 151 is controlled. Alternatively, if a NO answer is obtained in step 120, then the routine returns back to step 100. The operations in step 130 and 140 will be discussed in detail below with reference to FIGS. 4 and 5, respectively.

Figure 4:
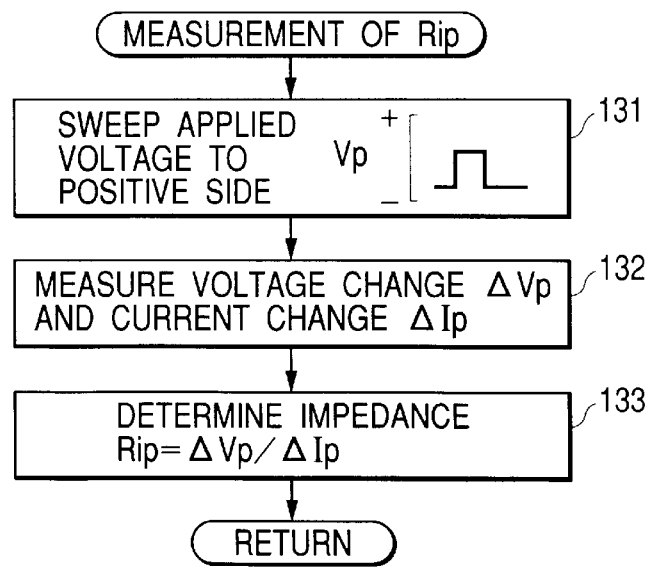
FIG. 4 is a flowchart of a subprogram to measure the impedance of a sensor element of a gas concentration senor which is used to control a power supply to a heater of a gas concentration sensor.

After entering step 130, the routine proceeds to step 131 of FIG. 4 wherein the voltage Vp to be applied to the pump cell 110 is shifted to a positive side in a single shot for several tens to one hundred μsec instantaneously.

The routine proceeds to step 132 wherein a change ΔVp in voltage Vp applied to the pump cell 110 and a change ΔIp in pump cell current Ip are measured. The routine proceeds to step 133 wherein the sensor element impedance Rip is calculated using the voltage change ΔVp and the current change ΔIp according to an equation of Rip=ΔVp/ΔIp. The routine returns back to the program of FIG. 3.

Figure 6:
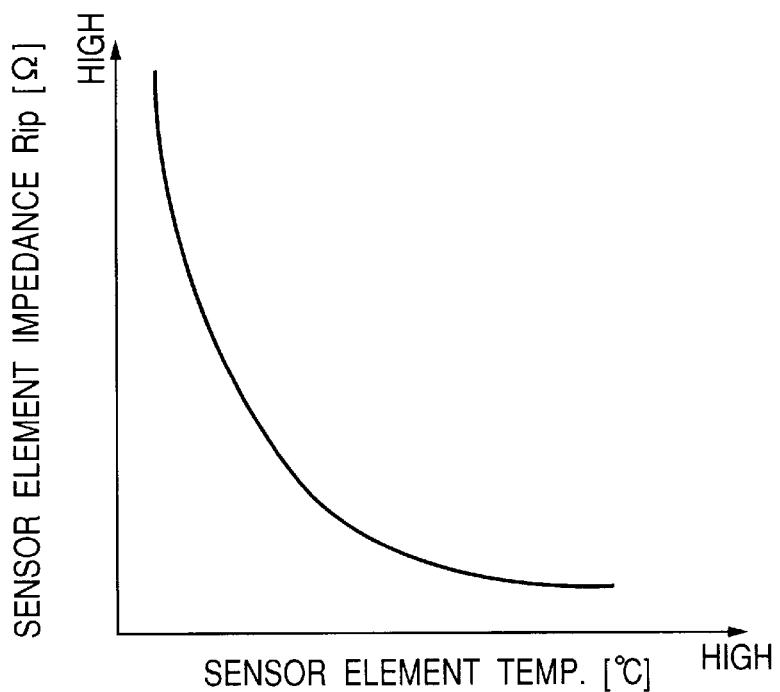
FIG. 6 is a map which shows a relation between the impedance and the temperature of a sensor element of a gas concentration sensor.

The sensor element impedance Rip bears a relation, as shown in a graph of FIG. 6, to the temperature of the sensor element. The graph shows that the sensor element impedance Rip increases greatly as the temperature of the sensor element decreases.

The control of power supply to the heater 151 performed in step 140 in FIG. 3 will be described below with reference to FIG. 5.

First, in step 141, it is determined whether a condition in which the control of power supply to the heater 151 should be initiated is met or not. For example, it is determined whether the sensor element impedance Rip is greater than or equal to 50 Ω or not. Usually, immediately after start-up of the engine, the temperature of the sensor element of the gas concentration sensor 100 is low, so that the sensor element impedance Rip is high. In this case, it is determined in step 141 that the control of power supply to the heater 151 should be initiated.

If a YES answer is obtained in step 141 meaning that the control of power supply to the heater 151 should be initiated, the routine proceeds to step 142 wherein a duty cycle-controlled signal, which will also be referred to as a heater power supply control signal below) is kept in duty cycle at 100% to supply the power to the heater 151 fully.

Alternatively, if the temperature of the sensor element has already risen, a NO answer is obtained in step 141. The routine, thus, proceeds to step 143. In following steps, a sensor element impedance target value Rtg is corrected as a function of a change in characteristic of the gas concentration sensor 100, and the power supply to the heater 151 is adjusted under feedback control. The correction of the sensor element impedance target value Rtg is achieved by look-up using a map listing a relation between the power supply to the heater 151 and the sensor element impedance.

Specifically, in step 143, the sensor element impedance Rip, as determined in the subprogram of FIG. 4, is read out of a memory. The routine proceeds to step 144 wherein from the heater voltage developed across the heater 151 and the heater current flowing through the heater 151 as determined in the heater control circuit 175, the power supply to the heater 151 is calculated.

Figure 7:
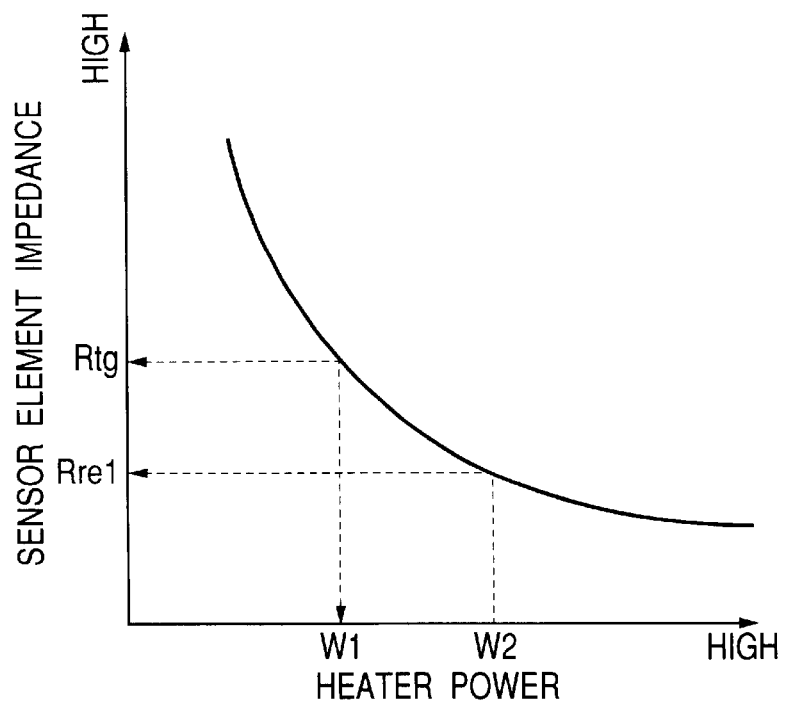
FIG. 7 is a map which shows a relation between the impedance of a sensor element of a gas concentration sensor and a power consumed in a heater built in a gas concentration sensor.

The routine proceeds to step 145 wherein a reference sensor element impedance Rre in an impedance-temperature characteristic that is one of fundamental characteristics exhibited by the gas concentration sensor 100 is determined as a function of power now applied to the heater 151 by look-up using a map shown in FIG. 7. The map shows a relation between the heater power and the reference sensor element impedance in the fundamental impedance-temperature characteristic of the gas concentration sensor 100 and indicates a reference value of the impedance of the sensor element (i.e., the pump cell 110 in this embodiment) of the gas concentration sensor 100 as a function of the power applied to the heater 151. In other words, the map represents the power required for the heater 151 to keep a specified value of the sensor element impedance constant. The map of FIG. 7 shows that when the power W2 is being supplied to the heater 151, the sensor element impedance is kept at a target value Rtg, and when the power actually consumed in the heater 151 is measured as W2, the impedance of the sensor element may be estimated as Rref1.

Figure 8:
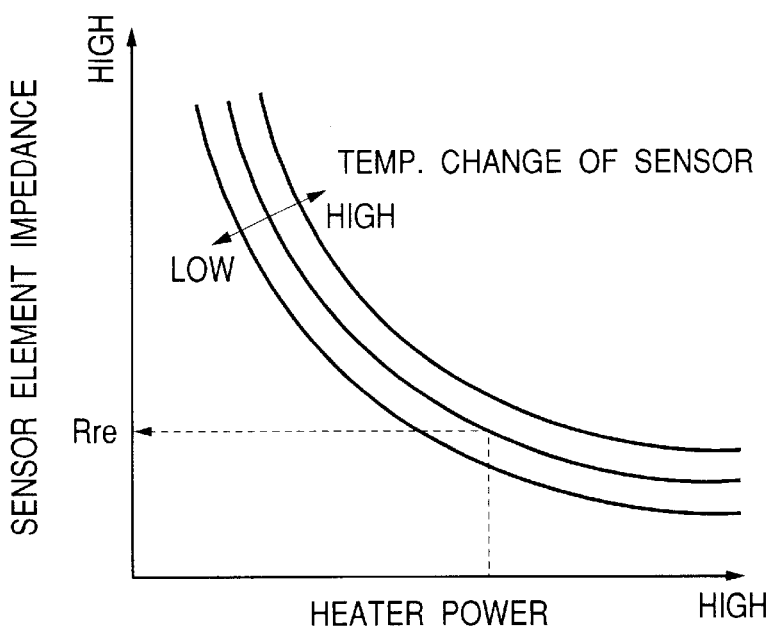
FIG. 8 is a map which lists relations between a reference sensor element impedance and a heater power in terms of a change in temperature of a gas concentration sensor arising from a change in temperature of exhaust gasses.

The impedance-heater power relation of FIG. 7 will change with a change in temperature of exhaust gasses caused by, for example, a change in burning state of the engine and a fuel cut. When such a temperature change is taken place, a map, as shown in FIG. 8, may alternatively be used. The map lists relations between the reference sensor element impedance and the heater power in terms of a change in temperature of the gas concentration sensor 100 arising from a change in temperature of the exhaust gasses. The degree to which the gas concentration sensor 100 is heated or a change in temperature of the gas concentration sensor 100 heated by the exhaust gasses may be determined as a function of the quantity (i.e., a flow rate) and temperature of the exhaust gasses estimated from the engine speed or load (or the position of an accelerator pedal or quantity of intake air) and the temperature of an engine coolant. The reference sensor element impedance Rre in the fundamental impedance-temperature characteristic of the gas concentration sensor 100 is determined as a function of the change in temperature of the gas concentration sensor 10. When the temperature of the gas concentration sensor 100 is elevated, it eliminates the need for heating the gas concentration sensor 100 through the heater 151. The heater power corresponding to the target sensor element impedance Rtg is, thus, decreased.

Subsequently, the routine proceeds to step 146 wherein the target sensor element impedance Rtg is corrected using the sensor element impedance Rip as derived in step 143 and the reference sensor element impedance Rre. The correction is achieved by subtracting the reference sensor element impedance Rre from the sensor element impedance Rip and adding a resulting difference to the target sensor element impedance Rtg.

Figure 9:
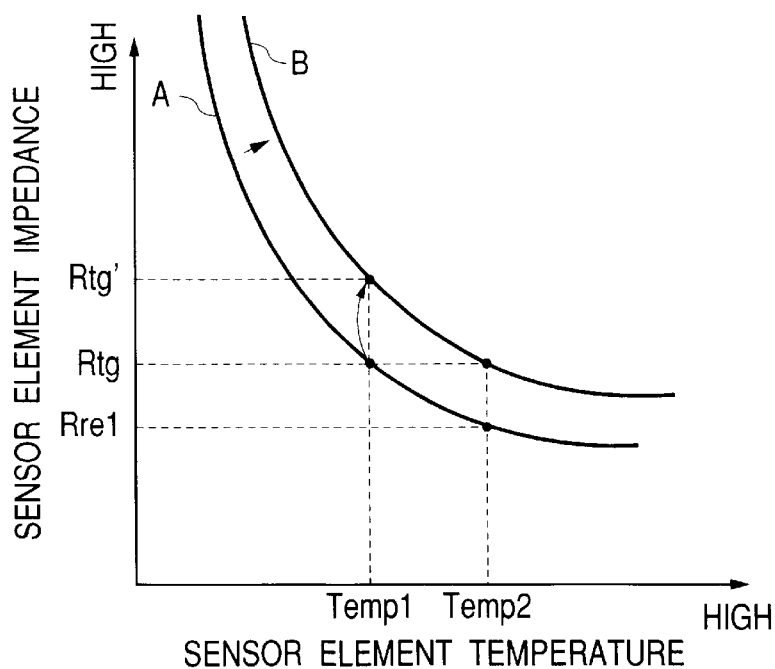
FIG. 9 is a graph which shows a fundamental impedance-temperature characteristic of a gas concentration sensor and a fundamental characteristic changed due to the deterioration of the gas concentration sensor.

The correction of the target sensor element impedance Rtg will be described in detail with reference to FIG. 9. In FIG. 9, a curve A indicates the fundamental impedance-temperature characteristic of the gas concentration sensor 100. A curve B indicates the fundamental characteristic changed due to, for example, the deterioration of the gas concentration sensor 100.

If the fundamental impedance-temperature characteristic A remains unchanged, the temperature of the sensor element of the gas concentration sensor 100 when the impedance of the sensor element is bought into agreement with the target value Rtg under feedback control will be a target one Temp 1. If the fundamental impedance-temperature characteristic is changed from A to B, the feedback control of the sensor element impedance may cause the temperature of the sensor element to be elevated to Temp 2. Thus, in this case, the reference sensor element impedance Rre in the fundamental impedance-temperature characteristic A is determined using the heater power W2, as shown in FIG. 7. A difference between the target sensor element impedance Rtg and the reference sensor element impedance Rre (i.e., Rtg−Rre) is determined as a correction value. The correction value is added to the target sensor element impedance Rtg to produce a target sensor element impedance Rtg', as shown in FIG. 9. Under the feedback control, the sensor element impedance Rip is usually converged on the target value Rtg (i.e., Rip=Rtg). The correction value is, thus, given by Rip−Rre1.

After completion of the above correction, the routine proceeds to step 147 wherein the duty cycle of the heater power supply control signal is determined as a function of a difference between the target sensor element impedance Rtg as corrected in step 146 and the sensor element impedance Rip as read out of the memory in step 143. For instance, a proportional term Gp, an integral term Gi, and a differential term Gd are determined using the following relations.

$Gp = Kp \cdot (Rip - Rtg)$ $Gi = Gi + Ki \cdot (Rip - Rtg)$ $Gd = Kd \cdot (Rip - R0)$ where R0 is the sensor element impedance Rip as measured one program cycle earlier, Kp is a proportional constant, Ki is an integral constant, and Kd is a differential constant.

The proportional term Gp, the integral term Gi, and the differential term Gd are summed up to determine the duty cycle of the heater power supply control signal (i.e., DUTY= Gp+Gi+Gd).

Subsequently, the routine returns back to the subprogram of FIG. 3.

As apparent from the above discussion, the target value of the sensor element impedance used as a control variable for controlling a power supply to the heater 151 is corrected using the fundamental impedance-temperature characteristic of the gas concentration sensor 100. This enables the power supply to the heater 151 to be performed regardless of a change in characteristic (i.e., the temperature) of the gas concentration sensor 100, which ensures a desired activated state of the pump cell 110 and the sensor cell 130, thus resulting in improved accuracy of measurement in the gas concentration sensor 100. Particularly, an output of the sensor cell 130 is very weak in level and sensitive to activation of the sensor cell 130. The above correction, thus, ensures the accuracy of measurement of concentration of NOx.

Figure 10:
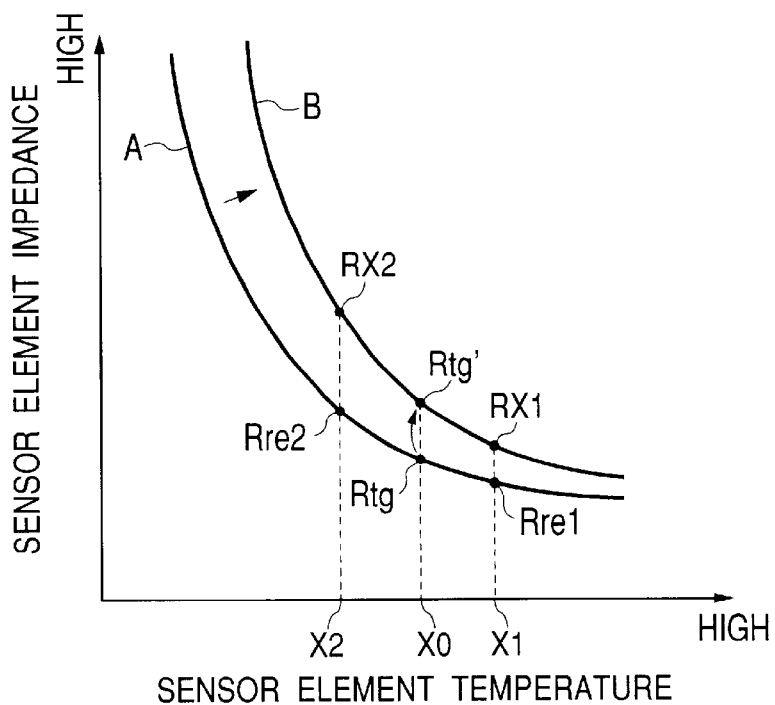
FIG. 10 is a graph which shows relations between the impedance and the temperature of a sensor element of a gas concentration sensor before and after a change in fundamental impedance-temperature characteristic of the gas concentration sensor.

The correction of the target sensor element impedance Rtg may alternatively be achieved in manners as discussed below with reference to FIGS. 10 and 11.

(1) The reference sensor element impedances Rre are determined which correspond to at least two temperatures of the sensor element defined across a target controlled temperature thereof. The target sensor element impedance Rtg is corrected based on the reference sensor element impedances Rre and the corresponding measured impedances Rip of the sensor element. Specifically, two temperatures X1 and X2, as shown in FIG. 10, are defined across a target controlled temperature X0 of the sensor element of the gas concentration sensor 100. The heater 151 is controlled to heat the sensor element up to the temperatures X1 and X2. The impedances RX1 and RX2 of the sensor element are measured at the temperatures X1 and X2. The reference sensor element impedances Rre1 and Rre2 in the fundamental impedance-temperature characteristics of the gas concentration sensor 100 which correspond to the temperatures X1 and X2 are determined. If the fundamental impedance-temperature characteristic is shifted from A to B, it will cause differences, as shown in the drawing, to be produced between the sensor element impedance RX1 and the reference sensor element impedance X1 and between the sensor element impedance RX2 and the reference sensor element impedance X2. The target sensor element impedance Rtg is corrected by adding a correction value of [(RX1−Rre1)/2+(RX2−Rre1)/2] to the target sensor element impedance Rtg to produce the target sensor element impedance Rtg'. The impedances of the sensor element corresponding to more than two temperatures of the sensor element may be used to determined the correction value.

Figure 11:
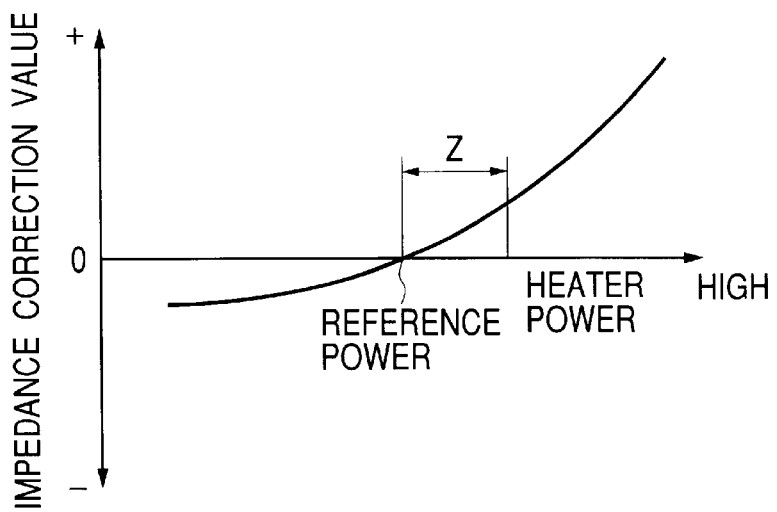
FIG. 11 is a map which shows an impedance correcting value in terms of a heater power.

(2) The correction value is determined by look-up using a map, as shown in FIG. 11, as a function of an actual power supplied or used in the heater 151 to correct the target sensor element impedance Rtg. Specifically, a curve in FIG. 11 indicates a reference power of the heater 151 required to bring the sensor element impedance into agreement with a target one. The correction value is determined as a function of a difference Z between the reference power and the actual power consumed in the heater 151. A change in temperature of the gas concentration sensor 100 by an external factor such as heating by the exhaust gasses may reflect on the curve of FIG. 11. An increased temperature of the gas concentration sensor 100 decreases the need for heating the gas concentration sensor 100 using the heater 151. In this case, the curve is shifted to the left, as viewed in the drawing, to reduce the reference power of the heater 151 as the degree to which the gas concentration sensor 100 is heated increases.

Figure 5:
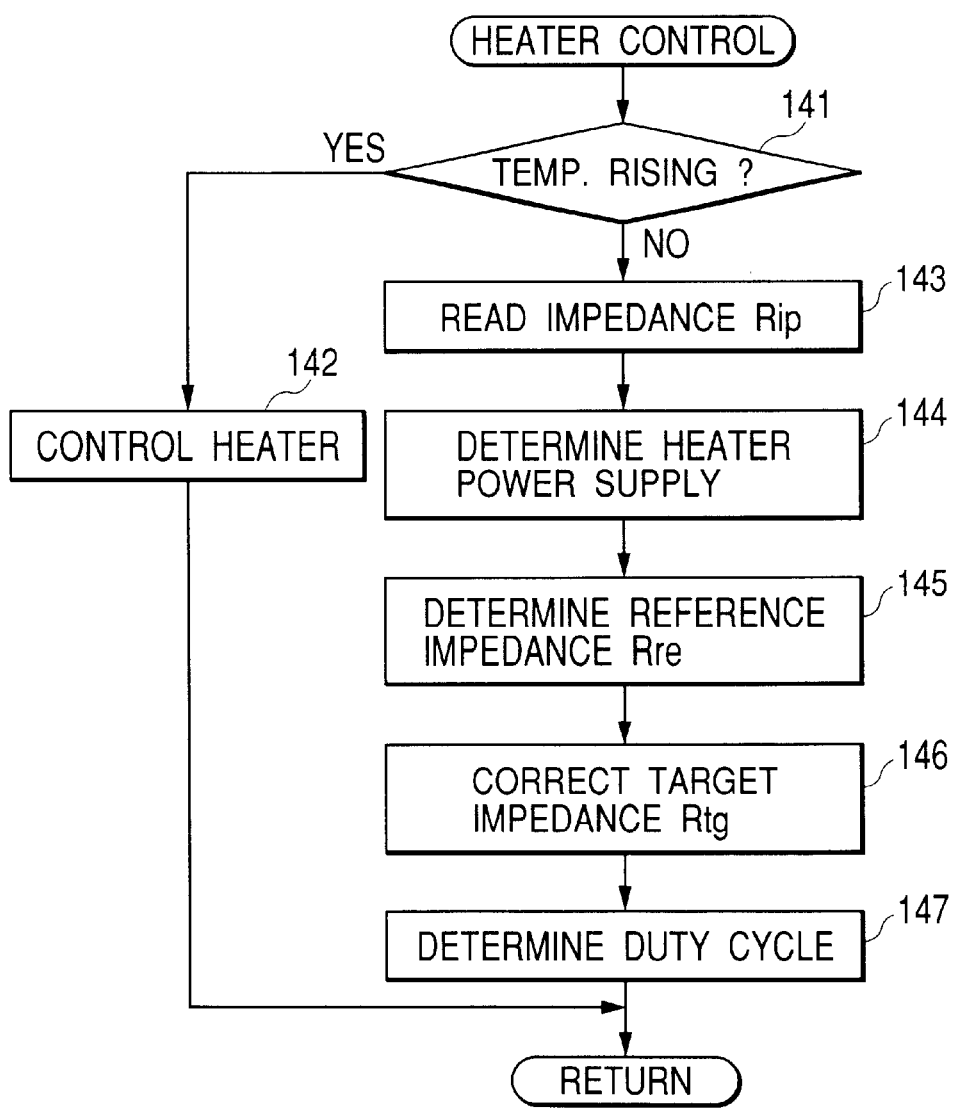
FIG. 5 is a flowchart of a subprogram performed to control a power supply to a heater built in a gas concentration sensor.

In a case where the target sensor element impedance Rtg is, as discussed in FIG. 5, corrected under condition that the external factor in changing the temperature of the gas concentration sensor 100 remains unchanged, it may be performed when the gas concentration sensor 100 is not heated by the exhaust gasses. For instance, the correction is made when the engine is at rest. In this case, it is unnecessary to consider the degree to which the gas concentration sensor 100 is heated.

The correction value derived in either of the above manners may be stored, in sequence, as a learning value in a RAM (i.e. a backup memory). After such learning values are derived, the fundamental impedance-temperature characteristic of the gas concentration sensor 100 is modified using the learning values for compensating for an error in controlling the power supply to the heater 151 arising from a change in characteristic of the gas concentration sensor 100 with time. This may be made when the engine is at rest.

Figure 12:
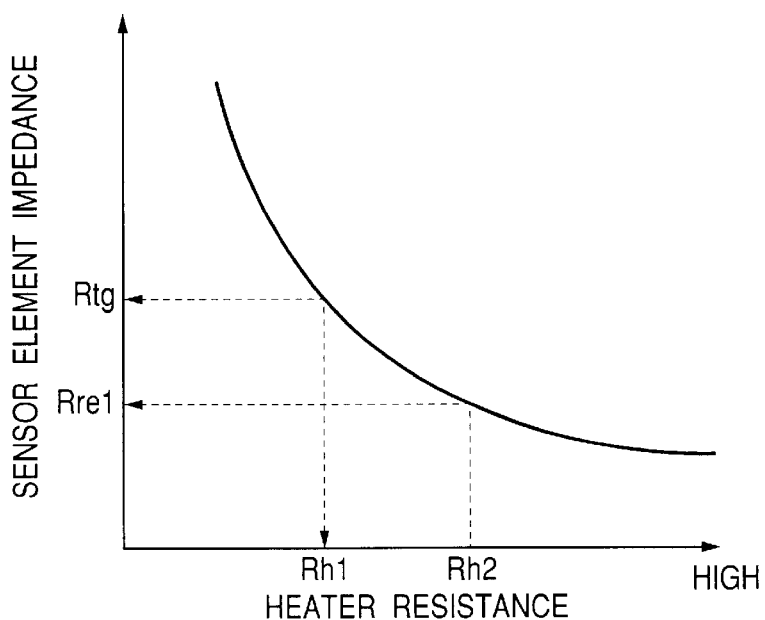
FIG. 12 is a map which shows a relation between a reference sensor element impedance and a resistance of a heater.

The microcomputer 170 may alternatively determine the resistance of the heater 151 to correct the target sensor element impedance Rtg. For instance, in step 144 of FIG. 5, the microcomputer 170 calculates the resistance of the heater 151 (=heater voltage/heater current) instead of the required power supply to the heater 151. In step 145, the reference sensor element impedance Rre in a fundamental impedance-resistance characteristic of the gas concentration sensor 100, as shown in FIG. 12, is determined as a function of the resistance of the heater 151. When the sensor element impedance Rip is kept at the target value Rtg, the resistance of the heater 151 has a value Rh1. If the resistance of the heater 151 shows a value Rh2, the reference sensor element impedance Rre may be determined as Rre1. The microcomputer 170 corrects in step 146 the target sensor element impedance Rtg by adding a difference between the sensor element impedance Rip as derived in step 143 and the reference sensor element impedance Rre to the target sensor element impedance Rtg.

Figure 13:
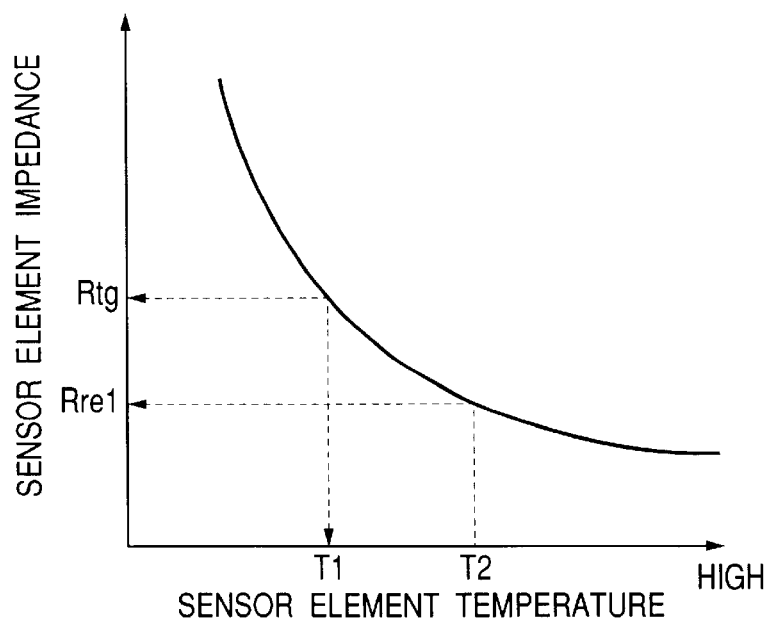
FIG. 13 is a map which shows a relation between a reference sensor element impedance and a temperature of a sensor element of a gas concentration sensor.

The microcomputer 170 may measure the temperature of the sensor element of the gas concentration sensor 100 to correct the target sensor element impedance Rtg. The determination of the temperature of the sensor element may be accomplished by installing a thermocouple on the solid electrolyte plate 141 and 142 to measure the temperature of the sensor element actually or estimating the temperature of the sensor element using an output of an exhaust gas temperature sensor indicating the temperature of exhaust gasses of the engine or an output of an exhaust gas flow rate sensor indicating the flow rate of the exhaust gasses. Use of the speed of the engine in addition to the temperature or flow rate of the exhaust gasses result in improved accuracy of determination of the temperature of the sensor element. Specifically, in step 144 of FIG. 5, the microcomputer 170 calculates the temperature of the sensor element instead of the required power supply to the heater 151. In step 145, the reference sensor element impedance Rre1 is determined using an impedance-temperature relation, as shown in FIG. 13, as a function of the temperature of the sensor element. When the sensor element impedance Rip is kept at the target value Rtg, the temperature of the sensor element has a value T2. If the temperature of the sensor element shows a value T2, the reference sensor element impedance Rre may be determined as Rre1. The microcomputer 170 corrects in step 146 the target sensor element impedance Rtg by adding a difference between the sensor element impedance Rip as derived in step 143 and the reference sensor element impedance Rre to the target sensor element impedance Rtg.

The sensor element impedance Rip, as discussed above, is the impedance of the pump cell 110 (i.e., the solid electrolyte plate 142), but however, the impedance of the sensor cell 130 may alternatively be used for controlling the power supply to the heater 151. Instead of the sensor element impedance Rip, the admittance that is the reciprocal of the impedance Rip may also be used. Such a resistance of the sensor element may be determined by changing the voltage or current applied to the solid electrolyte plate of either of the pump cell 110 and the sensor cell 130 and measuring changes in voltage appearing across the solid electrolyte plate and current flowing therethrough.

The microcomputer 170 may determine the degree of deterioration of the gas concentration sensor 100 as a function of the correction value used to correct the target sensor element impedance Rtg. Usually, when the gas concentration sensor 100 deteriorates or ages, it will cause the correction value to be increased. The degree of aging of the gas concentration sensor 100 may, thus, be determined as a function of the correction value. If the correction value exceeds a given threshold value, the microcomputer 170 may decide that the gas concentration sensor 100 has aged undesirably.

Figure 14A:
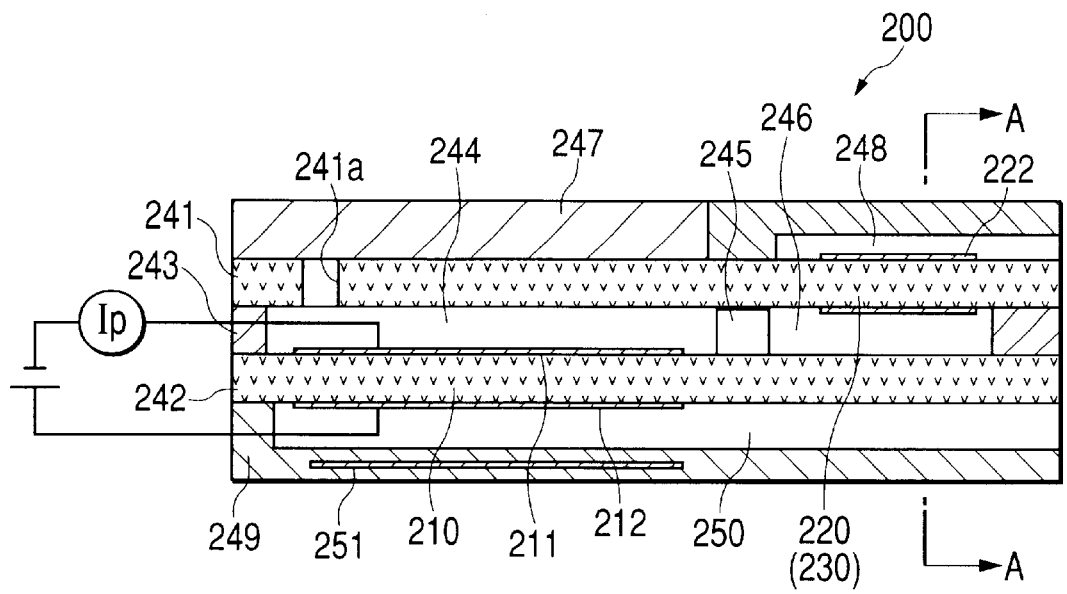
FIG. 14(a) is a longitudinal sectional view which shows a gas concentration sensor which may be employed in the gas concentration measuring apparatus of FIG. 1.
Figure 14B:
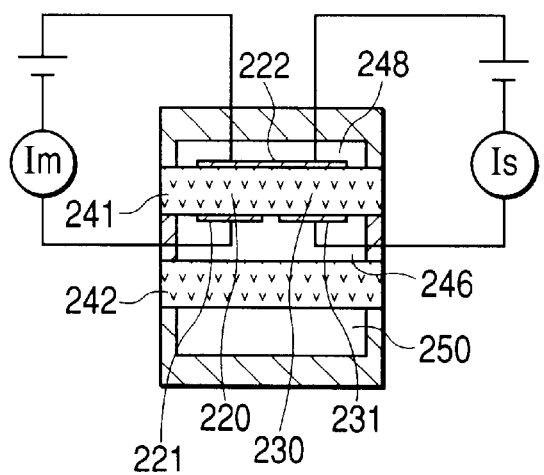
FIG. 14(b) is a lateral sectional view taken along the line A—A in FIG. 14(a).

FIGS. 14(a) and 14(b) show a gas concentration sensor 200 which may be employed in the gas concentration measuring apparatus of FIG. 1.

The gas concentration sensor 200 has a three-cell structure which is designed to measure the concentration of NOx and $O_2$ contained in exhaust gasses of the engine simultaneously.

The gas concentration sensor 200 includes generally solid electrolyte plates 241 and 242 made of an oxygen ion-conducting material. The solid electrolyte plates 241 and 242 are laid to overlap each other at a given interval through a spacer 243 made of an insulating material such as alumina. The solid electrolyte plate 241 has formed therein a pinhole 241a through which exhaust gasses flowing around the gas concentration sensor 200 are admitted into a first chamber 244. The first chamber 244 communicates with a second chamber 246 through an orifice 245 working as a diffusion path. On the solid electrolyte plate 241, a porous diffusion layer 247 is formed.

The solid electrolyte plate 242 has formed therein a pump cell 210 which is exposed to the first chamber 244. The pump cell 210 works to dissociate or ionize and pump thereinto oxygen molecules ($O_2$) contained the exhaust gasses admitted into the first chamber 244 and discharge them for measuring the concentration of oxygen ($O_2$) contained in the exhaust gasses and also to dissociate or ionize and pump oxygen molecules ($O_2$) within an air passage 250 into the first chamber 244 when the concentration of oxygen within the first chamber 244 is lower than a given level for keeping the concentration of oxygen within the first chamber 244 at the given level. The pump cell 210 has a pair of upper and lower electrodes 211 and 212 disposed on opposed surfaces of the solid electrolyte plate 242. The upper electrode 211 is exposed to the first chamber 244 and inactive with respect to NOx, that is, hardly decomposes NOx. The pump cell 210 works to pump $O_2$ molecules contained in the exhaust gasses out of the first chamber 244 and discharge them to the air passage 250 through the electrode 212.

A monitor cell 220 and a sensor cell 230 are also formed on the solid electrolyte plate 241. The monitor cell 220 and the sensor cell 230 are exposed to the second chamber 246. The monitor cell 220 works to produce an electromotive force or current upon application of the voltage as a function the concentration of oxygen ($O_2$) remaining within the second chamber 246. The sensor cell 230 serves to measure the concentration of NOx contained in the exhaust gasses having passed through the pump cell 210.

The monitor cell 220 and the sensor cell 230 are, as can be seen from FIG. 14(b), arranged in parallel at substantially the same location with respect to a flow of the exhaust gasses. The monitor cell 220 and the sensor cell 230 share an electrode 222 exposed to an air passage 248. Specifically, the monitor cell 220 is made up of the solid electrolyte plate 241, an electrode 221, and the common electrode 222. The sensor cell 230 is made up of the solid electrolyte plate 241, an electrode 231, and the common electrode 222. The electrode 221 of the monitor cell 220 is made of a noble metal such as Au-Pt which is inactive with respect to NOx, while the electrode 231 of the sensor cell 230 is made of a noble metal such as Pt which is active with respect to NOx.

An insulating layer 249 is disposed on a lower surface, as viewed in FIG. 14(a), of the solid electrolyte plate 242 to define the air passage 250. The insulating layer 249 has embedded therein a heater 251 for heating the whole of the sensor 200 up to a desired activation temperature.

In operation, when exhaust gasses containing $O_2$, NOx, $CO_2$, and $H_2O$ enter the first chamber 244 through the porous diffusion layer 247 and the pinhole 241a and are passing through the pump cell 210, application of voltage to the pump cell 210 through the electrodes 211 and 212 causes the exhaust gasses to undergo dissociation, so that the oxygen ($O_2$) is pumped into or out of the first chamber 244 as a function of the concentration of oxygen ($O_2$) within the first chamber 244 so as to keep the concentration of oxygen within the first chamber 244 constant. Since the upper electrode 211 of the pump cell 210 is, as described above, made of a metal which hardly decomposes NOx, when the concentration of oxygen within the first chamber 244 is higher than a desired level, only $O_2$ molecules within the first chamber 244 are ionized by the pump cell 210 without decomposing NOx, which are, in turn, discharged to the air passage 250. This causes a current (i.e., the pump cell current) to be produced in the pump cell 210 as a function of the oxygen content of the exhaust gasses.

The $O_2$ molecules in the exhaust gasses are usually not dissociated by the pump cell 210 completely, so that residual $O_2$ molecules flows into the second chamber 246 and reach the monitor cell 220. The application of given voltage to the monitor cell 220 through the electrodes 221 and 222 causes an output (i.e., the monitor cell current) to be produced as a function of the concentration of the residual oxygen. The application of given voltage to the sensor cell 230 through the electrodes 231 and 222 causes NOx molecules contained in the exhaust gasses to be decomposed or reduced, so that oxygen ions are produced and discharged to the air passage 248, thereby causing a current (i.e., the sensor cell current) to flow through the sensor 230 as a function of the concentration of NOx within the second chamber 246.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

Instead of the gas concentration sensors 100 and 200, another type of gas concentration sensor having a four-cell or a five-cell structure may be employed. Specifically, a gas concentration sensor having at least a first cell working to pump oxygen out of gasses and a second cell working to measure the concentration of a specified gas component may be used. The sensor element impedance used to control a power supply to the heater may be measured from any of the cells.

The gas concentration measuring apparatus as discussed above uses the gas concentration sensor 100 or 200 designed to measure the concentrations of NOx and $O_2$, but may employ another type of gas sensor which has a first cell working to pump $O_2$ out of gasses and a second cell working to dissociate hydro carbon (HC) and/or carbon monoxide (CO) from the gasses from which $O_2$ has been pumped by the first cell to measure the concentration of HC and/or CO.

What is claimed is:

1. A heater control apparatus used for a gas concentration sensor which includes a gas chamber, a first cell working to pump thereinto oxygen molecules contained in gasses admitted into the gas chamber and discharge the pumped oxygen molecules, a second cell working to determine a concentration of a specified oxygen containing gas component contained in the gasses having passed through the first cell, a solid electrolyte member on which at least one of the first and second cells is disposed, and a heater heating the first and the second cells, comprising:

a sensor element resistance value determining circuit working to applying one of a varying voltage and a varying current to the solid electrolyte member and measuring resulting changes in voltage appearing across the solid electrolyte member and current flowing through the solid electrolyte member to determine a resistance value of a sensor element including the solid electrolyte member;

a heater control circuit controlling a power supply to the heater as a function of a difference between the resistance value determined by said sensor element resistance value determining circuit and a target resistance value;

a heater power determining circuit determining a power supplied to the heater; and a correcting circuit working to determine a reference resistance value of the sensor element as a function of the power determined by said heater power determining circuit based on a predetermined fundamental relation between a power used in the heater and a resistance value of the sensor element, said correcting circuit correcting the target resistance value as a function of the reference resistance value.

2. A heater control apparatus as set forth in claim 1, wherein said correcting circuit corrects the target resistance value based on the reference resistance value and the resistance value determined by said sensor element resistance value determining circuit.

3. A heater control apparatus as set forth in claim 1, wherein said correcting circuit corrects the target resistance value as a function of a difference between the reference resistance value and the resistance value determined by said sensor element resistance value determining circuit.

4. A heater control apparatus as set forth in claim 1, wherein said correcting circuit reflects an external factor of a change in temperature of the sensor element in an environmental condition of the gas concentration sensor in correcting the target resistance value.

5. A heater control apparatus as set forth in claim 1, wherein said correcting circuits corrects the target resistance value under condition that an external factor of a change in temperature of the sensor element is unchanged.

6. A heater control apparatus as set forth in claim 1, wherein said gas concentration sensor is installed in an exhaust pipe of an engine and used in an engine control system working to detect exhaust gasses of the engine through said gas concentration sensor, and wherein said correcting circuit corrects the target resistance value under condition that the engine is at rest.

7. A heater control apparatus as set forth in claim 1, wherein the degree to which the correcting circuit corrects the target resistance value is stored in a backup memory as a learning value.

8. A heater control apparatus as set forth in claim 1, wherein a measure of deterioration of said gas concentration sensor is determined based on the degree to which the correcting circuit corrects the target resistance value.

9. A heater control apparatus used for a gas concentration sensor including a gas chamber, a first cell working to pump thereinto oxygen molecules contained in gasses admitted into the gas chamber and discharge the pumped oxygen molecules, a second cell working to determine a concentration of a specified oxygen containing gas component contained in the gasses having passed through the first cell, a solid electrolyte member on which at least one of the first and second cells is disposed, and a heater heating the first and the second cells, comprising:

a sensor element resistance value determining circuit working to applying one of a varying voltage and a varying current to the solid electrolyte member and measuring resulting changes in voltage appearing across the solid electrolyte member and current flowing through the solid electrolyte member to determine a resistance value of a sensor element including the solid electrolyte member;

a heater control circuit controlling a power supply to the heater as a function of a difference between the resistance value determined by said sensor element resistance value determining circuit and a target resistance value;

a heater resistance determining circuit determining a resistance value of the heater; and a correcting circuit working to determine a reference resistance value of the sensor element as a function of the resistance value determined by said heater resistance determining circuit based on a predetermined fundamental relation between a resistance value of the heater and a resistance value of the sensor element, said correcting circuit correcting the target resistance value as a function of the reference resistance value.

10. A heater control apparatus as set forth in claim 9, wherein said correcting circuit corrects the target resistance value as a function of a difference between the reference resistance value and the resistance value determined by said sensor element resistance value determining circuit.

11. A heater control apparatus as set forth in claim 9, wherein said correcting circuit reflects an external factor of a change in temperature of the sensor element in an environmental condition of the gas concentration sensor in correcting the target resistance value.

12. A heater control apparatus as set forth in claim 9, wherein said correcting circuits corrects the target resistance value under condition that an external factor of a change in temperature of the sensor element is unchanged.

13. A heater control apparatus as set forth in claim 9, wherein said gas concentration sensor is installed in an exhaust pipe of an engine and used in an engine control system working to detect exhaust gasses of the engine through said gas concentration sensor, and wherein said correcting circuit corrects the target resistance value under condition that the engine is at rest.

14. A heater control apparatus as set forth in claim 9, wherein the degree to which the correcting circuit corrects the target resistance value is stored in a backup memory as a learning value.

15. A heater control apparatus as set forth in claim 9, wherein a measure of deterioration of said gas concentration sensor is determined based on the degree to which the correcting circuit corrects the target resistance value.

16. A heater control apparatus used for a gas concentration sensor including a gas chamber, a first cell working to pump thereinto oxygen molecules contained in gasses admitted into the gas chamber and discharge the pumped oxygen molecules, a second cell working to determine a concentration of a specified oxygen containing gas component contained in the gasses having passed through the first cell, a solid electrolyte member on which at least one of the first and second cells is disposed, and a heater heating the first and the second cells, comprising:

a sensor element resistance value determining circuit working to applying one of a varying voltage and a varying current to the solid electrolyte member and measuring resulting changes in voltage appearing across the solid electrolyte member and current flowing through the solid electrolyte member to determine a resistance value of a sensor element including the solid electrolyte member;

a heater control circuit controlling a power supply to the heater as a function of a difference between the resistance value determined by said sensor element resistance value determining circuit and a target resistance value;

a sensor element temperature determining circuit determining a temperature of the sensor element; and a correcting circuit working to determine a reference resistance value of the sensor element as a function of the temperature determined by said sensor element temperature determining circuit based on a predetermined fundamental relation between a temperature of the sensor element and a resistance value of the sensor element, said correcting circuit correcting the target resistance value as a function of the reference resistance value.

17. A heater control apparatus as set forth in claim 16, wherein said gas concentration sensor is installed in an exhaust pipe of an engine to measure and used in an engine control system designed to detect exhaust gasses of the engine, and wherein said sensor element temperature determining circuit determines, as the temperature of the sensor element; one of an actual temperature of the sensor element and an estimate thereof based on one of a temperature and a flow rate of the exhaust gasses.

18. A heater control apparatus as set forth in claim 16, wherein said heater control circuit controls the power supply to the heater to bring a temperature of the sensor element into agreement with a target controlled temperature, and wherein said sensor element temperature determining circuit determines two temperatures of the sensor element defined across the target controlled temperature, and said correcting circuit determines two reference resistance values corresponding to the two temperatures of the sensor element by look-up using said predetermined fundamental relation and corrects the target resistance value using the two temperatures of the sensor element and the two reference resistance values.

19. A heater control apparatus as set forth in claim 16, wherein said correcting circuit corrects the target resistance value as a function of a difference between the reference resistance value and the resistance value determined by said sensor element resistance value determining circuit.

20. A heater control apparatus as set forth in claim 16, wherein said correcting circuit reflects an external factor of a change in temperature of the sensor element in an environmental condition of the gas concentration sensor in correcting the target resistance value.

21. A heater control apparatus as set forth in claim 16, wherein said correcting circuits corrects the target resistance value under condition that an external factor of a change in temperature of the sensor element is unchanged.

22. A heater control apparatus as set forth in claim 16, wherein said gas concentration sensor is installed in an exhaust pipe of an engine and used in an engine control system working to detect exhaust gasses of the engine through said gas concentration sensor, and wherein said correcting circuit corrects the target resistance value under condition that the engine is at rest.

23. A heater control apparatus as set forth in claim 16, wherein the degree to which the correcting circuit corrects the target resistance value is stored in a backup memory as a learning value.

24. A heater control apparatus as set forth in claim 16, wherein a measure of deterioration of said gas concentration sensor is determined based on the degree to which the correcting circuit corrects the target resistance value.

* * * * *